United States Patent
Brown et al.

(10) Patent No.: US 7,381,048 B2
(45) Date of Patent: Jun. 3, 2008

(54) STENTS WITH PROFILES FOR GRIPPING A BALLOON CATHETER AND MOLDS FOR FABRICATING STENTS

(75) Inventors: Daniel Gene Brown, Temecula, CA (US); Hector Onelio Torres, Temecula, CA (US); Mark Harris, Temecula, CA (US); Chris Andrews, Lake Elsinore, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 501 days.

(21) Appl. No.: 11/105,004

(22) Filed: Apr. 12, 2005

(65) Prior Publication Data

US 2006/0229695 A1   Oct. 12, 2006

(51) Int. Cl.
*B29C 49/48* (2006.01)
(52) U.S. Cl. .................. 425/522; 425/392; 425/470
(58) Field of Classification Search .......... 425/522, 425/392, 470
See application file for complete search history.

(56) References Cited

U.S. PATENT DOCUMENTS

| | | | |
|---|---|---|---|
| 3,687,135 A | 8/1972 | Stroganov et al. | |
| 3,839,743 A | 10/1974 | Schwarcz | |
| 3,900,632 A | 8/1975 | Robinson | |
| 4,104,410 A | 8/1978 | Malecki | |
| 4,110,497 A | 8/1978 | Hoel | |
| 4,321,711 A | 3/1982 | Mano | |
| 4,346,028 A | 8/1982 | Griffith | |
| 4,596,574 A | 6/1986 | Urist | |
| 4,599,085 A | 7/1986 | Riess et al. | |
| 4,612,009 A | 9/1986 | Drobnik et al. | |
| 4,633,873 A | 1/1987 | Dumican et al. | |
| 4,656,083 A | 4/1987 | Hoffman et al. | |
| 4,718,907 A | 1/1988 | Karwoski et al. | |
| 4,722,335 A | 2/1988 | Vilasi | |
| 4,723,549 A | 2/1988 | Wholey et al. | |
| 4,732,152 A | 3/1988 | Wallsten et al. | |
| 4,733,665 A | 3/1988 | Palmaz | |
| 4,739,762 A | 4/1988 | Palmaz | |
| 4,740,207 A | 4/1988 | Kreamer | |
| 4,743,252 A | 5/1988 | Martin, Jr. et al. | |
| 4,768,507 A | 9/1988 | Fischell et al. | |
| 4,776,337 A | 10/1988 | Palmaz | |
| 4,800,882 A | 1/1989 | Gianturco | |

(Continued)

FOREIGN PATENT DOCUMENTS

DE      44 07 079      9/1994

(Continued)

OTHER PUBLICATIONS

U.S. Appl. No. 10/317,435, filed Dec. 11, 2002, Hossainy et al.

(Continued)

*Primary Examiner*—Robert B. Davis
*Assistant Examiner*—Marissa W Chaet
(74) *Attorney, Agent, or Firm*—Squire, Sanders & Dempsey LLP

(57) ABSTRACT

Embodiments of stents having profiles that improve gripping of the stent on a stent delivery system are provided. Additionally, embodiments of molds for fabricating the stents are provided.

11 Claims, 7 Drawing Sheets

U.S. PATENT DOCUMENTS

| | | | |
|---|---|---|---|
| 4,816,339 A | 3/1989 | Tu et al. | |
| 4,818,559 A | 4/1989 | Hama et al. | |
| 4,850,999 A | 7/1989 | Planck | |
| 4,877,030 A | 10/1989 | Beck et al. | |
| 4,878,906 A | 11/1989 | Lindemann et al. | |
| 4,879,135 A | 11/1989 | Greco et al. | |
| 4,886,062 A | 12/1989 | Wiktor | |
| 4,902,289 A | 2/1990 | Yannas | |
| 4,977,901 A | 12/1990 | Ofstead | |
| 4,994,298 A | 2/1991 | Yasuda | |
| 5,019,090 A | 5/1991 | Pinchuk | |
| 5,028,597 A | 7/1991 | Kodama et al. | |
| 5,059,211 A | 10/1991 | Stack et al. | |
| 5,062,829 A | 11/1991 | Pryor et al. | |
| 5,084,065 A | 1/1992 | Weldon et al. | |
| 5,085,629 A | 2/1992 | Goldberg et al. | |
| 5,100,429 A | 3/1992 | Sinofsky et al. | |
| 5,104,410 A | 4/1992 | Chowdhary | |
| 5,108,417 A | 4/1992 | Sawyer | |
| 5,108,755 A | 4/1992 | Daniels et al. | |
| 5,112,457 A | 5/1992 | Marchant | |
| 5,123,917 A | 6/1992 | Lee | |
| 5,156,623 A | 10/1992 | Hakamatsuka et al. | |
| 5,163,951 A | 11/1992 | Pinchuk et al. | |
| 5,163,952 A | 11/1992 | Froix | |
| 5,163,958 A | 11/1992 | Pinchuk | |
| 5,167,614 A | 12/1992 | Tessmann et al. | |
| 5,192,311 A | 3/1993 | King et al. | |
| 5,197,977 A | 3/1993 | Hoffman, Jr. et al. | |
| 5,234,456 A | 8/1993 | Silvestrini | |
| 5,234,457 A | 8/1993 | Andersen | |
| 5,236,447 A | 8/1993 | Kubo et al. | |
| 5,279,594 A | 1/1994 | Jackson | |
| 5,282,860 A | 2/1994 | Matsuno et al. | |
| 5,289,831 A | 3/1994 | Bosley | |
| 5,290,271 A | 3/1994 | Jernberg | |
| 5,306,286 A | 4/1994 | Stack et al. | |
| 5,306,294 A | 4/1994 | Winston et al. | |
| 5,328,471 A | 7/1994 | Slepian | |
| 5,330,500 A | 7/1994 | Song | |
| 5,342,348 A | 8/1994 | Kaplan | |
| 5,342,395 A | 8/1994 | Jarrett et al. | |
| 5,342,621 A | 8/1994 | Eury | |
| 5,356,433 A | 10/1994 | Rowland et al. | |
| 5,383,925 A | 1/1995 | Schmitt | |
| 5,385,580 A | 1/1995 | Schmitt | |
| 5,389,106 A | 2/1995 | Tower | |
| 5,399,666 A | 3/1995 | Ford | |
| 5,423,885 A | 6/1995 | Williams | |
| 5,441,515 A | 8/1995 | Khosravi et al. | |
| 5,443,458 A | 8/1995 | Eury et al. | |
| 5,443,500 A | 8/1995 | Sigwart | |
| 5,455,040 A | 10/1995 | Marchant | |
| 5,464,650 A | 11/1995 | Berg et al. | |
| 5,502,158 A | 3/1996 | Sinclair et al. | |
| 5,514,379 A | 5/1996 | Weissleder et al. | |
| 5,527,337 A | 6/1996 | Stack et al. | |
| 5,545,408 A | 8/1996 | Trigg et al. | |
| 5,554,120 A | 9/1996 | Chen et al. | |
| 5,556,413 A | 9/1996 | Lam | |
| 5,578,046 A | 11/1996 | Liu et al. | |
| 5,578,073 A | 11/1996 | Haimovich et al. | |
| 5,591,199 A | 1/1997 | Porter et al. | |
| 5,591,607 A | 1/1997 | Gryaznov et al. | |
| 5,593,403 A | 1/1997 | Buscemi | |
| 5,593,434 A | 1/1997 | Williams | |
| 5,599,301 A | 2/1997 | Jacobs et al. | |
| 5,599,922 A | 2/1997 | Gryaznov et al. | |
| 5,605,696 A | 2/1997 | Eury et al. | |
| 5,607,442 A | 3/1997 | Fischell et al. | |
| 5,607,467 A | 3/1997 | Froix | |
| 5,618,299 A | 4/1997 | Khosravi et al. | |
| 5,629,077 A | 5/1997 | Turnlund et al. | |
| 5,631,135 A | 5/1997 | Gryaznov et al. | |
| 5,632,771 A | 5/1997 | Boatman et al. | |
| 5,632,840 A | 5/1997 | Campbell | |
| 5,637,113 A | 6/1997 | Tartaglia et al. | |
| 5,649,977 A | 7/1997 | Campbell | |
| 5,667,767 A | 9/1997 | Greff et al. | |
| 5,667,796 A | 9/1997 | Otten | |
| 5,670,558 A | 9/1997 | Onishi et al. | |
| 5,693,085 A | 12/1997 | Buirge et al. | |
| 5,700,286 A | 12/1997 | Tartaglia et al. | |
| 5,707,385 A | 1/1998 | Williams | |
| 5,711,763 A | 1/1998 | Nonami et al. | |
| 5,716,981 A | 2/1998 | Hunter et al. | |
| 5,725,549 A | 3/1998 | Lam | |
| 5,726,297 A | 3/1998 | Gryaznov et al. | |
| 5,728,751 A | 3/1998 | Patnaik | |
| 5,733,326 A | 3/1998 | Tomonto et al. | |
| 5,733,330 A | 3/1998 | Cox | |
| 5,733,564 A | 3/1998 | Lehtinen | |
| 5,733,925 A | 3/1998 | Kunz et al. | |
| 5,741,881 A | 4/1998 | Patnaik | |
| 5,756,457 A | 5/1998 | Wang et al. | |
| 5,756,476 A | 5/1998 | Epstein et al. | |
| 5,765,682 A | 6/1998 | Bley et al. | |
| 5,766,204 A | 6/1998 | Porter et al. | |
| 5,766,239 A | 6/1998 | Cox | |
| 5,766,710 A | 6/1998 | Turnlund et al. | |
| 5,769,883 A | 6/1998 | Buscemi et al. | |
| 5,780,807 A | 7/1998 | Saunders | |
| 5,800,516 A | 9/1998 | Fine et al. | |
| 5,811,447 A | 9/1998 | Kunz et al. | |
| 5,824,049 A | 10/1998 | Ragheb et al. | |
| 5,830,178 A | 11/1998 | Jones et al. | |
| 5,830,461 A | 11/1998 | Billiar | |
| 5,830,879 A | 11/1998 | Isner | |
| 5,833,651 A | 11/1998 | Donovan et al. | |
| 5,834,582 A | 11/1998 | Sinclair et al. | |
| 5,836,962 A | 11/1998 | Gianotti | |
| 5,837,313 A | 11/1998 | Ding et al. | |
| 5,837,835 A | 11/1998 | Gryaznov et al. | |
| 5,840,083 A | 11/1998 | Braach-Maksvytis | |
| 5,851,508 A | 12/1998 | Greff et al. | |
| 5,853,408 A | 12/1998 | Muni | |
| 5,854,207 A | 12/1998 | Lee et al. | |
| 5,855,612 A | 1/1999 | Ohthuki et al. | |
| 5,855,618 A | 1/1999 | Patnaik et al. | |
| 5,858,746 A | 1/1999 | Hubbell et al. | |
| 5,865,814 A | 2/1999 | Tuch | |
| 5,868,781 A | 2/1999 | Killion | |
| 5,873,904 A | 2/1999 | Ragheb et al. | |
| 5,874,101 A | 2/1999 | Zhong et al. | |
| 5,874,109 A | 2/1999 | Ducheyne et al. | |
| 5,874,165 A | 2/1999 | Drumheller | |
| 5,876,743 A | 3/1999 | Ibsen et al. | |
| 5,877,263 A | 3/1999 | Patnaik et al. | |
| 5,879,713 A | 3/1999 | Roth et al. | |
| 5,888,533 A | 3/1999 | Dunn | |
| 5,891,192 A | 4/1999 | Murayama et al. | |
| 5,897,955 A | 4/1999 | Drumheller | |
| 5,906,759 A | 5/1999 | Richter | |
| 5,914,182 A | 6/1999 | Drumheller | |
| 5,916,870 A | 6/1999 | Lee et al. | |
| 5,922,005 A | 7/1999 | Richter et al. | |
| 5,942,209 A | 8/1999 | Leavitt et al. | |
| 5,948,428 A | 9/1999 | Lee et al. | |
| 5,954,744 A | 9/1999 | Phan et al. | |
| 5,957,975 A | 9/1999 | Lafont et al. | |
| 5,965,720 A | 10/1999 | Gryaznov et al. | |
| 5,971,954 A | 10/1999 | Conway et al. | |
| 5,976,182 A | 11/1999 | Cox | |
| 5,980,564 A | 11/1999 | Stinson | |

| | | | | | | |
|---|---|---|---|---|---|---|
| 5,980,928 | A | 11/1999 | Terry | 6,461,632 | B1 | 10/2002 | Gogolewski |
| 5,980,972 | A | 11/1999 | Ding | 6,464,720 | B2 | 10/2002 | Boatman et al. |
| 5,981,568 | A | 11/1999 | Kunz et al. | 6,479,565 | B1 | 11/2002 | Stanley |
| 5,986,169 | A | 11/1999 | Gjunter | 6,485,512 | B1 | 11/2002 | Cheng |
| 5,997,468 | A | 12/1999 | Wolff et al. | 6,492,615 | B1 | 12/2002 | Flanagan |
| 6,010,445 | A | 1/2000 | Armini et al. | 6,494,908 | B1 | 12/2002 | Huxel et al. |
| 6,015,541 | A | 1/2000 | Greff et al. | 6,495,156 | B2 | 12/2002 | Wenz et al. |
| 6,042,875 | A | 3/2000 | Ding et al. | 6,511,748 | B1 | 1/2003 | Barrows |
| 6,048,964 | A | 4/2000 | Lee et al. | 6,517,888 | B1 | 2/2003 | Weber |
| 6,051,648 | A | 4/2000 | Rhee et al. | 6,527,801 | B1 | 3/2003 | Dutta |
| 6,056,993 | A | 5/2000 | Leidner et al. | 6,537,589 | B1 | 3/2003 | Chae et al. |
| 6,060,451 | A | 5/2000 | DiMaio et al. | 6,539,607 | B1 | 4/2003 | Fehring et al. |
| 6,066,156 | A | 5/2000 | Yan | 6,540,774 | B1 | 4/2003 | Cox et al. |
| 6,071,266 | A | 6/2000 | Kelley | 6,540,777 | B2 | 4/2003 | Stenzel |
| 6,074,659 | A | 6/2000 | Kunz et al. | 6,554,854 | B1 | 4/2003 | Flanagan |
| 6,080,177 | A | 6/2000 | Igaki et al. | 6,561,788 | B1 * | 5/2003 | Gaudoin .................... 425/522 |
| 6,080,488 | A | 6/2000 | Hostettler et al. | 6,565,599 | B1 | 5/2003 | Hong et al. |
| 6,083,258 | A | 7/2000 | Yadav | 6,569,191 | B1 | 5/2003 | Hogan |
| 6,093,463 | A | 7/2000 | Thakrar | 6,569,193 | B1 | 5/2003 | Cox et al. |
| 6,096,070 | A | 8/2000 | Ragheb et al. | 6,572,672 | B2 | 6/2003 | Yadav et al. |
| 6,096,525 | A | 8/2000 | Patnaik | 6,574,851 | B1 | 6/2003 | Mirizzi |
| 6,099,562 | A | 8/2000 | Ding et al. | 6,585,755 | B2 | 7/2003 | Jackson et al. |
| 6,103,230 | A | 8/2000 | Billiar et al. | 6,592,614 | B2 | 7/2003 | Lenker et al. |
| 6,107,416 | A | 8/2000 | Patnaik et al. | 6,592,617 | B2 | 7/2003 | Thompson |
| 6,110,188 | A | 8/2000 | Narciso, Jr. | 6,613,072 | B2 | 9/2003 | Lau et al. |
| 6,113,629 | A | 9/2000 | Ken | 6,626,939 | B1 | 9/2003 | Burnside et al. |
| 6,117,979 | A | 9/2000 | Hendriks et al. | 6,635,269 | B1 | 10/2003 | Jennissen |
| 6,120,536 | A | 9/2000 | Ding et al. | 6,645,243 | B2 | 11/2003 | Vallana et al. |
| 6,120,904 | A | 9/2000 | Hostettler et al. | 6,656,162 | B2 | 12/2003 | Santini, Jr. et al. |
| 6,121,027 | A | 9/2000 | Clapper et al. | 6,664,335 | B2 | 12/2003 | Krishnan |
| 6,125,523 | A | 10/2000 | Brown et al. | 6,666,214 | B2 | 12/2003 | Canham |
| 6,127,173 | A | 10/2000 | Eckstein et al. | 6,667,049 | B2 | 12/2003 | Janas et al. |
| 6,129,761 | A | 10/2000 | Hubbell | 6,669,723 | B2 | 12/2003 | Killion et al. |
| 6,129,928 | A | 10/2000 | Sarangapani et al. | 6,676,697 | B1 | 1/2004 | Richter |
| 6,150,630 | A | 11/2000 | Perry et al. | 6,679,980 | B1 | 1/2004 | Andreacchi |
| 6,153,252 | A | 11/2000 | Hossainy et al. | 6,689,375 | B1 | 2/2004 | Wahlig et al. |
| 4,776,337 | A | 12/2000 | Palmaz | 6,695,920 | B1 | 2/2004 | Pacetti et al. |
| 6,159,951 | A | 12/2000 | Karpeisky et al. | 6,706,273 | B1 | 3/2004 | Roessler |
| 6,160,084 | A | 12/2000 | Langer et al. | 6,709,379 | B1 | 3/2004 | Brandau et al. |
| 6,165,212 | A | 12/2000 | Dereume et al. | 6,719,934 | B2 | 4/2004 | Stinson |
| 6,166,130 | A | 12/2000 | Rhee et al. | 6,719,989 | B1 | 4/2004 | Matsushima et al. |
| 6,169,170 | B1 | 1/2001 | Gryaznov et al. | 6,720,402 | B2 | 4/2004 | Langer et al. |
| 6,171,609 | B1 | 1/2001 | Kunz | 6,746,773 | B2 | 6/2004 | Llanos et al. |
| 6,174,330 | B1 | 1/2001 | Stinson | 6,752,826 | B2 | 6/2004 | Holloway et al. |
| 6,177,523 | B1 | 1/2001 | Reich et al. | 6,753,007 | B2 | 6/2004 | Haggard et al. |
| 6,183,505 | B1 | 2/2001 | Mohn, Jr. et al. | 6,764,505 | B1 | 7/2004 | Hossainy et al. |
| 6,187,045 | B1 | 2/2001 | Fehring et al. | 6,818,063 | B1 | 11/2004 | Kerrigan |
| 6,210,715 | B1 | 4/2001 | Starling et al. | 6,846,323 | B2 | 1/2005 | Yip et al. |
| 6,224,626 | B1 | 5/2001 | Steinke | 2001/0044652 | A1 | 11/2001 | Moore |
| 6,228,845 | B1 | 5/2001 | Donovan et al. | 2002/0002399 | A1 | 1/2002 | Huxel et al. |
| 6,240,616 | B1 | 6/2001 | Yan | 2002/0004060 | A1 | 1/2002 | Heublein et al. |
| 6,245,076 | B1 | 6/2001 | Yan | 2002/0004101 | A1 | 1/2002 | Ding et al. |
| 6,245,103 | B1 | 6/2001 | Stinson | 2002/0062148 | A1 | 5/2002 | Hart |
| 6,248,344 | B1 | 6/2001 | Ylanen et al. | 2002/0065553 | A1 | 5/2002 | Weber |
| 6,251,135 | B1 | 6/2001 | Stinson et al. | 2002/0077690 | A1 | 6/2002 | Wang |
| 6,251,142 | B1 | 6/2001 | Bernacca et al. | 2002/0099406 | A1 | 7/2002 | St. Germain |
| 6,273,913 | B1 | 8/2001 | Wright et al. | 2002/0111590 | A1 | 8/2002 | Davila et al. |
| 6,281,262 | B1 | 8/2001 | Shikinami | 2002/0116050 | A1 | 8/2002 | Kocur |
| 6,284,333 | B1 | 9/2001 | Wang et al. | 2002/0138133 | A1 | 9/2002 | Lenz et al. |
| 6,287,332 | B1 | 9/2001 | Bolz et al. | 2002/0161114 | A1 | 10/2002 | Gunatillake et al. |
| 6,290,721 | B1 | 9/2001 | Heath | 2003/0033001 | A1 | 2/2003 | Igaki |
| 6,293,966 | B1 | 9/2001 | Frantzen | 2003/0093107 | A1 | 5/2003 | Parsonage et al. |
| 6,303,901 | B1 | 10/2001 | Perry et al. | 2003/0100865 | A1 | 5/2003 | Santini, Jr. et al. |
| 6,312,459 | B1 | 11/2001 | Huang et al. | 2003/0105518 | A1 | 6/2003 | Dutta |
| 6,327,772 | B1 | 12/2001 | Zadno-Azizi et al. | 2003/0105530 | A1 | 6/2003 | Pirhonen |
| 4,733,665 | C2 | 1/2002 | Palmaz | 2003/0171053 | A1 | 9/2003 | Sanders |
| 6,375,826 | B1 | 4/2002 | Wang et al. | 2003/0187495 | A1 | 10/2003 | Cully et al. |
| 6,379,381 | B1 | 4/2002 | Hossainy et al. | 2003/0208259 | A1 | 11/2003 | Penhasi |
| 6,387,121 | B1 | 5/2002 | Alt | 2003/0209835 | A1 | 11/2003 | Chun et al. |
| 6,388,043 | B1 | 5/2002 | Langer et al. | 2003/0226833 | A1 | 12/2003 | Shapovalov et al. |
| 6,395,326 | B1 | 5/2002 | Castro et al. | 2003/0236565 | A1 | 12/2003 | Fifer |
| 6,409,761 | B1 | 6/2002 | Jang | 2004/0093077 | A1 | 5/2004 | White et al. |
| 6,423,092 | B2 | 7/2002 | Datta et al. | 2004/0098095 | A1 | 5/2004 | Burnside et al. |

| | | | |
|---|---|---|---|
| 2004/0111149 A1 | 6/2004 | Stinson | |
| 2004/0127970 A1 | 7/2004 | Weber | |
| 2004/0143317 A1 | 7/2004 | Stinson et al. | |
| 2004/0167610 A1 | 8/2004 | Fleming III | |
| 2004/0249435 A1 | 12/2004 | Andreas | |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 97/40780 | 11/1997 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/49973 | 8/2000 |
| WO | WO 00/64506 | 11/2000 |
| WO | WO 01/01890 | 1/2001 |
| WO | WO 2004/023985 | 3/2004 |

OTHER PUBLICATIONS

Anonymous, *Bioabsorbable stent mounted on a catheter having optical coherence tomography capabilities*, Research Disclosure, Sep. 2004, pp. 1159-1162.

Ansari, *Tubal Reanastomosis Using Absorbable Stent*, International Journal of Fertility, vol. 23, No. 4, pp. 242-243 (1978).

Ansari, *End-to-end tubal anastomosis using an absorbable stent*, Fertility and Sterility, vol. 32(2), pp. 197-201 (Aug. 1979).

Bull, *Parylene Coating for Medical Applications*, Medical Product Manufacturing News 1 pg. (Mar. 1993).

Casper et al., *Fiber-Reinforced Absorbable Composite for Orthopedic Surgery*, Polymeric Materials Science and Engineering, 53: pp. 497-501 (1985).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules 2, pp. 430-441 (2001).

Feng-Chun et al., *Assessment of Tissue Blood Flow Following Small Artery Welding with an Intraluminal Dissolvable Stent*, Microsurgery, vol. 19(3), pp. 148-152 (1999).

Hahn et al., *Glow Discharge Polymers as Coatings for Implanted Devices*, ISA, pp. 109-111 (1981).

Hahn et al., *Biocompatibility of Glow-Discharge-Polymerized Films and Vacuum-Deposited Parylene*, J Applied Polymer Sci, 38, pp. 55-64 (1984).

Kelley et al., *Totally Resorbable High-Strength Composite Material*, Advances in Biomedical Polymers, 35, pp. 75-85 (1987).

Kubies et al., *Microdomain Structure In polylactide-block-poly(ethylene oxide) copolymer films*, Biomaterials 21, pp. 529-536 (2000).

Kutryk et al., *Coronary Stenting: Current Perspectives*, a companion to the Handbook of Coronary Stents 16 pgs. (1999).

Mauduit et al., *Hydrolytic degradation of films prepared from blends of high and low molecular weight poly(DL-lactic acid)s*, J. Biomed. Mater. Res. v. 30, pp. 201-207 (1996).

Martin et al., *Enhancing the biological activity of immobilized osteopontin using a type-1 collagen affinity coating*, J. Biomed. Mater Res 70A, pp. 10-19 (2004).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., 1(4), pp. 438-448 (Jul./Aug. 1990).

Nichols et al., *Electrical Insulation of Implantable Devices by Composite Polymer Coatings*, ISA Transactions, 26(4), pp. 15-18 (1987).

Peuster et al., *A novel approach to temporary stenting: degradable cardiovascular stents produced from corrodible metal-results 6-18 months after implantation into New Zealand white rabbits*, Heart 86, pp. 563-569 (2001).

Pietrzak et al., *Bioresorbable implants—practical considerations*, Bone v. 19, No. 1, Supplement Jul. 1996: 109S-119S.

Pietrzak et al., *Bioabsorbable Fixation Devices: Status for the Craniomaxillofacial Surgeon*, J. Craniofaxial Surg. 2, pp. 92-96 (1997).

von Recum et al., *Degradation of polydispersed poly(L-lactic acid) to modulate lactic acid release*, Biomaterials 16, pp. 441-445 (1995).

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, 79(2), pp. 445-457 (Feb. 1989).

Schmidt et al., *Long-Term Implants of Parylene-C Coated Microelectrodes*, Med & Biol Eng & Comp, 26(1), pp. 96-101 (Jan. 1988).

Spagnuolo et al., *Gas 1 is induced by VE-cadherin and vascular endothelial growth factor and inhibits endothelial cell apoptosis*, Blood 103, pp. 3005-3012 (2004).

Tamai et al., *Initial and 6-Month Results of Biodegradable Poly-l-Lactic Acid Coronary Stents in Humans*, Circulation , pp. 399-404 (2000).

Tsui et al., *Biodegradable Polymeric Stents*, Current Interventional Cardiology Reports 3, pp. 10-17 (2001).

Völkel et al., *Targeting of immunoliposomes to endothelial cells using a single -chain Fv fragment directed against human endoglin(CD105)*, Biochemica et Biophysica Acta 1663, pp. 158-166 (2004).

Yau et al. Modern Size-Exclusion Liquid Chromatography, Wiley-Interscience Publication, (1979).

U.S. Appl. No. 10/879,328, filed Jun. 28, 2004, Gale et al.
U.S. Appl. No. 10/956,759, filed Sep. 30, 2004, Durcan.
U.S. Appl. No. 10/956,910, filed Sep. 30, 2004, Huang et al.

U.S. Appl. No. 10/956,911, filed Sep. 30, 2004, Durcan.

* cited by examiner

STENTS WITH PROFILES FOR GRIPPING A BALLOON CATHETER AND MOLDS FOR FABRICATING STENTS

TECHNICAL FIELD

This invention relates generally to stent delivery apparatuses, and more particularly, but not exclusively, to a stent for gripping a balloon catheter and a mold for fabricating the stent.

BACKGROUND

Blood vessel occlusions are commonly treated by mechanically enhancing blood flow in the affected vessels, such as by employing a stent. Stents act as scaffoldings, functioning to physically hold open and, if desired, to expand the wall of affected vessels. Typically stents are capable of being compressed, so that they can be inserted through small lumens via catheters, and then expanded to a larger diameter once they are at a desired location. Examples in the patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

Conventionally, stents are delivered to the desired location by crimping the stent tightly onto a balloon catheter and transporting the crimped stent/balloon catheter combination to the desired location through a patient's vasculature. Alternatively or in addition to the crimping, the balloon catheter is expanded to contact the inner diameter of the stent. At the desired location, the balloon catheter is expanded, thereby expanding the stent to contact the inner diameter of the patient's artery. The balloon catheter is then deflated and removed from the vasculature.

Since the stent and catheter travel through the patient's vasculature, the stent must have a small diameter so that it can pass through small lumens of the patient's vasculature. Secure attachment to the catheter is desirable so that the stent does not prematurely detach from the catheter. The stent should also be sufficiently flexibility to travel through curvatures in the patient's vasculature.

However, conventional crimping techniques can be uneven, leading to sharp edges on the crimped stent that can damage or get caught on the patient's vasculature during delivery. Further, crimping can decrease flexibility of the stent, making it hard to deliver the stent through curvatures in the patient's vasculature.

If the balloon catheter is expanded before delivery, the balloon catheter may cause excessive expansion of the stent, thereby making it hard to transport the stent through the patient's vasculature (e.g., cross tight lesions). Further, expansion of the balloon catheter can cause the distal and proximal ends of the stent to expand further than the rest of the stent, causing the distal and proximal ends to have upward tapered edges that can get caught in the patient's vasculature, thereby decreasing deliverability.

Accordingly, improved methods and devices are desirable for gripping a stent to a balloon catheter that reduce or eliminated the deficiencies mentioned above.

SUMMARY

Certain embodiments of the invention may include a stent mounted on a delivery system having a proximal section tapering inward to a proximal end of the stent and a distal section tapering inward to a distal end of the stent. The tapered sections may be adapted to improve the attachment of the stent to the delivery system and to facilitate the delivery of the mounted device into and through a bodily lumen.

Further embodiments of the invention may include a stent mounted on a delivery system having a section with a cross-section that oscillates in size between a proximal section and a distal section. The oscillating cross section may be adapted to improve flexibility during delivery of the mounted stent.

In other embodiments of the invention, a mold for a stent may include a mold member having a projection into a proximal section of a mold bore of the mold member. The projection may be configured to mold a tapered section at a proximal end of a stent mounted on a delivery system. The tapered section may be adapted to improve the attachment of the stent to the delivery system and facilitate the delivery of the mounted stent into and through a bodily lumen.

Additional embodiments of the invention may include a mold for a stent having a mold member with a mold bore configured to mold a stent mounted on a delivery system, the mold bore having a proximal section tapering inward to a proximal end of the mold bore and a distal section tapering inward to a distal end of the mold bore. The tapered sections may be adapted to mold tapered sections of the stent that improve the attachment of the stent to the delivery system and that facilitate the delivery of the mounted stent into and through a bodily lumen.

In another embodiment of the invention, a mold for a stent may include a mold member with a mold bore having a section with a cross-section that oscillates in size between a proximal section and a distal section. The oscillating cross section may be configured to mold a stent mounted on a delivery system to have an oscillating cross section. The oscillating cross section of the stent may improve flexibility of the mounted stent during delivery.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DETAILED DESCRIPTION

The following description is provided to enable any person having ordinary skill in the art to make and use the invention, and is provided in the context of a particular application and its requirements. Various modifications to the embodiments will be readily apparent to those skilled in the art, and the generic principles defined herein may be applied to other embodiments and applications without departing from the spirit and scope of the invention. Thus, the present invention is not intended to be limited to the embodiments shown, but is to be accorded the widest scope consistent with the principles, features and teachings disclosed herein.

Figure 1:
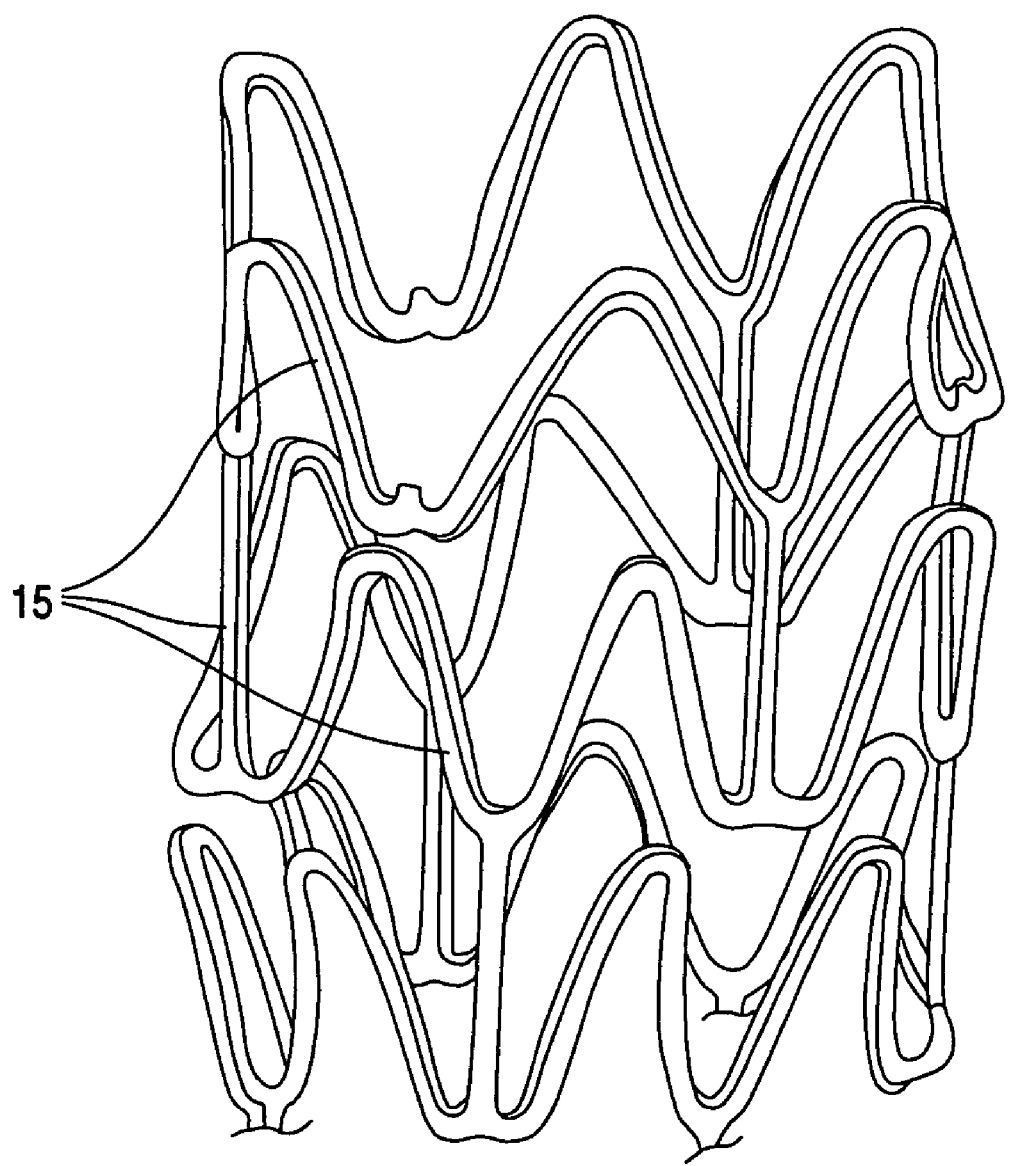
FIG. 1 is an illustration of a stent.

The term "implantable medical device" is intended to include self-expandable stents, balloon-expandable stents, stent-grafts, and grafts. The structural pattern of the device can be of virtually any design. A stent, for example, may include a pattern or network of interconnecting structural elements or struts. FIG. 1 depicts an example of a three-dimensional view of a stent 10. The stent may have a pattern that includes a number of interconnecting elements or struts 15. The embodiments disclosed herein are not limited to stents or to the stent pattern illustrated in FIG. 1. The embodiments are easily applicable to other patterns and other devices. The variations in the structure of patterns are virtually unlimited. As shown in FIG. 1 the geometry or shape of a stent varies throughout its structure.

In some embodiments, a stent may be formed from a tube by laser cutting the pattern of struts in the tube. The stent may also be formed by laser cutting a polymeric or metallic sheet, rolling the pattern into the shape of the cylindrical stent, and providing a longitudinal weld to form the stent. Other methods of forming stents are well known and include chemically etching a sheet and rolling and then welding it to form the stent. A polymeric or metallic wire may also be coiled to form the stent. The stent may be formed by injection molding of a thermoplastic or reaction injection molding of a thermoset polymeric material. Filaments of the compounded polymer may be extruded or melt spun. These filaments can then be cut, formed into ring elements, welded closed, corrugated to form crowns, and then the crowns welded together by heat or solvent to form the stent. Lastly, hoops or rings may be cut from tubing stock, the tube elements stamped to form crowns, and the crowns connected by welding or laser fusion to form the stent.

Additionally, an implantable medical device may be configured to degrade after implantation by fabricating the device either partially or completely from biodegradable polymers. Polymers can be biostable, bioabsorbable, biodegradable, or bioerodable. Biostable refers to polymers that are not biodegradable. The terms biodegradable, bioabsorbable, and bioerodable, as well as degraded, eroded, and absorbed, are used interchangeably and refer to polymers that are capable of being completely eroded or absorbed when exposed to bodily fluids such as blood and can be gradually resorbed, absorbed, and/or eliminated by the body.

Furthermore, a biodegradable device may be intended to remain in the body for a duration of time until its intended function of, for example, maintaining vascular patency and/or drug delivery is accomplished. For biodegradable polymers used in coating applications, after the process of degradation, erosion, absorption, and/or resorption has been completed, no polymer will remain on the stent. In some embodiments, very negligible traces or residue may be left behind. The duration is typically in the range of six to twelve months.

Representative examples of polymers that may be used to fabricate embodiments of implantable medical devices disclosed herein include, but are not limited to, poly(N-acetylglucosamine) (Chitin), Chitosan, poly(3-hydroxyvalerate), poly(lactide-co-glycolide), poly(3-hydroxybutyrate), poly(4-hydroxybutyrate), poly(3-hydroxybutyrate-co-3-hydroxyvalerate), polyorthoester, polyanhydride, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(glycolide-co-caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating embodiments of implantable medical devices disclosed herein include ethylene vinyl alcohol copolymer (commonly known by the generic name EVOH or by the trade name EVAL), poly(butyl methacrylate), poly(vinylidene fluoride-co-hexafluoropropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, poly(vinyl acetate), styrene-isobutylene-styrene triblock copolymers, and polyethylene glycol.

In addition, a device may be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

As discussed above, delivery of a stent is facilitated by a secure attachment of the stent to a delivery system and by flexibility of the stent. A small profile stent (crimped tightly) with a small stent diameter allows for secure attachment and eases transport through narrow lumen passages. However, decreasing a profile of a stent also decreases flexibility of the stent. Conversely, a larger profile stent (expanded stent) with a large stent diameter allows for greater flexibility. However, a large profile makes transport through narrow lumen passages more difficult.

The negative effects on delivery of a small and large profile can be reconciled by using a stent having both large and small profile sections. The small profile sections facilitate secure attachment, while the large profile sections facilitate flexibility. Furthermore, a small profile section at or proximate to a stent end that is a leading end or edge during delivery may be particularly helpful in facilitating delivery. Various embodiments of implantable medical devices, such as stents, having at least these characteristic are disclosed herein.

Certain embodiments of an implantable medical device, such as a radially expandable stent, mounted on a delivery system may include a proximal section tapering inward to a proximal end of the stent and a distal section tapering inward to a distal end of the stent. The tapered sections may be adapted to improve the attachment of the stent to the delivery system. Additionally, the tapered section may facilitate the delivery of the mounted device into and through a bodily lumen.

Facilitating delivery may include facilitating smooth communication of device through a lumen without substantially limiting the ability of device to bend around curvatures in the lumen. Facilitating delivery also may include improving a grip or attachment of the device on the delivery system since. A tapered portion of a device may tend to strengthen a grip of the device on the delivery system. Thus a tapered section may inhibit or prevent disengagement of the device from the delivery system.

In one embodiment, at least a portion of the stent may have a cross-section that is circular or substantially circular. A delivery system may be, for example, a balloon catheter for delivering a stent.

Figure 2:
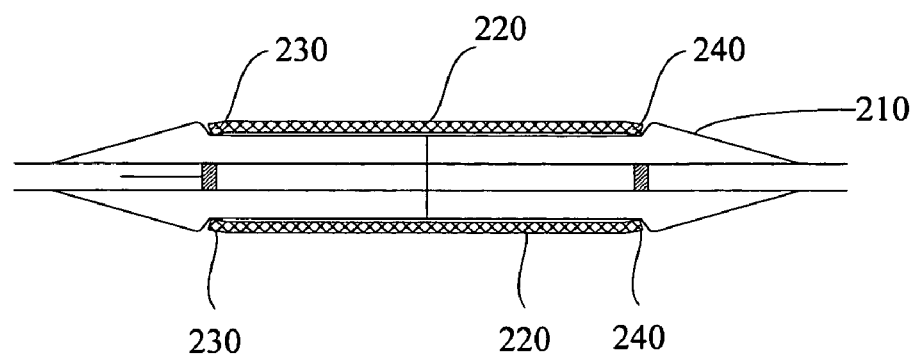
FIG. 2 is a diagram illustrating a stent installed on a balloon catheter using the mold of FIG. 7.

As an illustration, FIG. 2 depicts an axial cross section of a stent 220 having tapered sections 230 and 240 at a distal end and a proximal end, respectively. Stent 220 may be installed on balloon catheter 210 using a mold 600 in FIG. 7. Installed stent 220 has a profile in which proximal section 230 and distal section 240 of stent 220 exhibit an inward taper, instead of straight or outward taper outwards, as with conventional stents.

Accordingly, stent 220 can more easily travel through a patient's vasculature during delivery and is less likely to get caught in or damage the vasculature. Further, since the majority of stent 220 has an expanded profile, stent 220 can still track curvatures in the vasculature.

Additionally, the profile also causes stent 220 to "hug" or grip balloon catheter 210, thereby increasing the ability of stent 220 to stay mounted to the balloon catheter during delivery (until balloon 210 is deflated).

In some embodiments, an implantable medical device, such as a stent, mounted on a delivery system may have a proximal section tapering inward to a proximal end of the stent and a distal section tapering inward to a distal end of the stent. The tapered sections may be adapted to improve the attachment of the stent to the delivery system and to facilitate the delivery of the mounted device into and through a bodily lumen.

Figure 3:
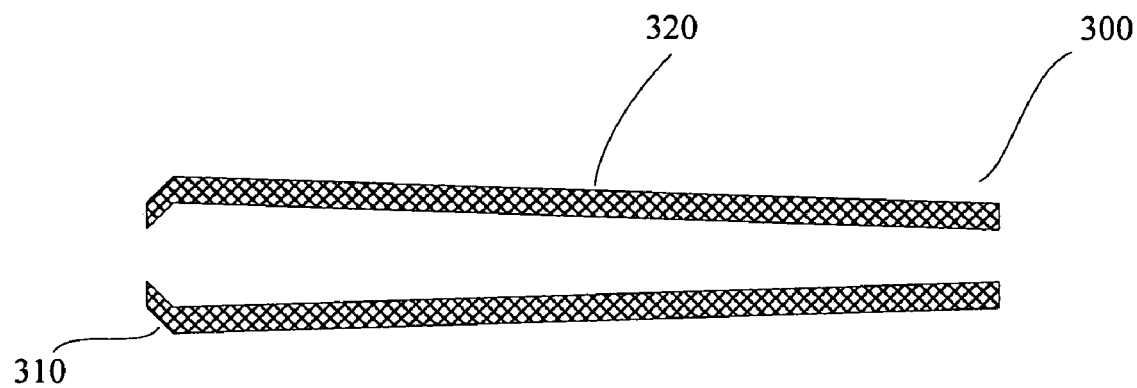
FIG. 3 is a diagram illustrating a stent formed using the mold of FIG. 9.

In one embodiment, a device may have profile that tapers inward relatively uniformly between the proximal section and the distal section. Thus, the mounted stent may have an "arrow-like" shape. As an illustration, FIG. 3 depicts a stent 300 having a proximal section 310 that is tapered inward toward a proximal end. Stent 300 also has a section 320 that tapers inward relatively uniformly from the proximal section to a distal end to adopt an arrow-like shape. Stent 300 may be installed on a balloon catheter using a mold 800 in FIG. 9.

As indicated above, a small profile at a leading end or edge of a stent is particularly advantageous. To facilitate delivery, the distal end may be a leading edge during delivery. A "leading edge" is the edge of stent that faces the direction of travel during implantation of the stent.

In another embodiment, the proximal section may taper inward relatively uniformly from an intermediate point between the proximal end and the distal end to the proximal end. The distal section may taper inward relatively uniformly from the intermediate point to the distal end.

Figure 4:
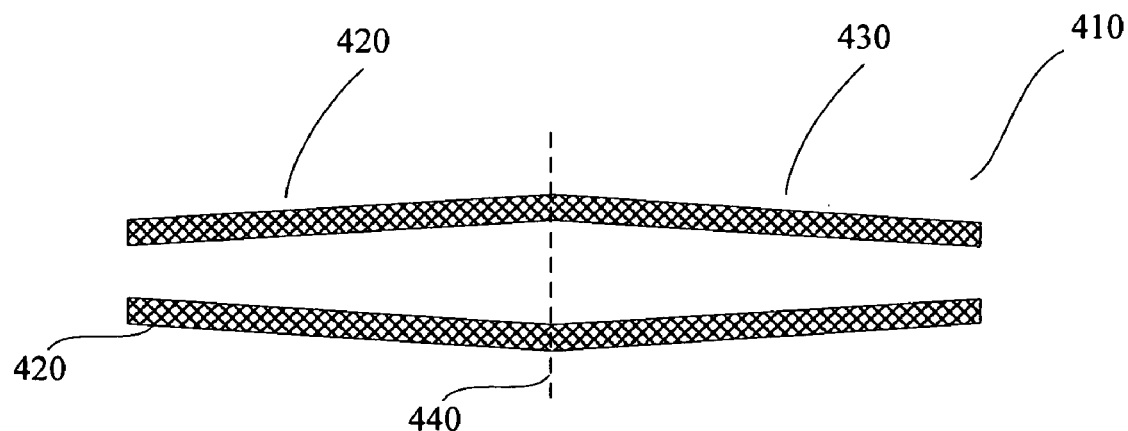
FIG. 4 is a diagram illustrating a stent formed using the mold of FIG. 10.

As an illustration, FIG. 4 depicts a stent 410 having a proximal section 420 and a distal section 430 that taper inward relatively uniformly from an intermediate point 440. Stent 410 has a diameter that gradually increases from a minimum value at the proximal and distal ends to a maximum value at intermediate point 440. Intermediate point 440, for example, may be approximately midway between the proximal and distal ends of the stent. Stent 410 may be installed on a balloon catheter using a mold 1000 in FIG. 10.

In one embodiment, a diameter of a stent that is about 6 mm long and about 0.041 inches in diameter at its midpoint can have a diameter at the distal and proximal ends between about 0.037 inches to about 0.038 inches.

The profile of stents 220, 300, and 410 facilitate a firm attachment of the stents to a balloon catheter, while maintaining flexibility. Further, the stents may travel more easily through tight lumens due to the small diameter at the ends as compared to conventional stents. Further, the stents are less likely to get caught or damage the patient's vasculature because the stents lack upwardly tapered ends as conventional stents may have after balloon catheter expansion.

In further embodiments, an implantable medical device, such as a stent mounted on a delivery system may include a section having a cross-section that oscillates in size between a proximal section and a distal section. The oscillating cross section may be adapted to improve flexibility during delivery of the mounted stent. Such a stent may have a "wave-like" profile with peaks and troughs.

The section of a stent having a wave-like profile may have at least one narrow region alternating with at least one wide region. At least a portion of the at least one narrow region is in contact with a surface of the delivery system. In addition, at least a portion of the at least one wide region may not be in contact with the surface of the delivery system. Thus, narrow regions may allow the stent to grip a balloon catheter. In addition, the wide regions allow the stent to flex and bend as the mounted stent passes through curved and/or narrow vasculature.

Figure 5:
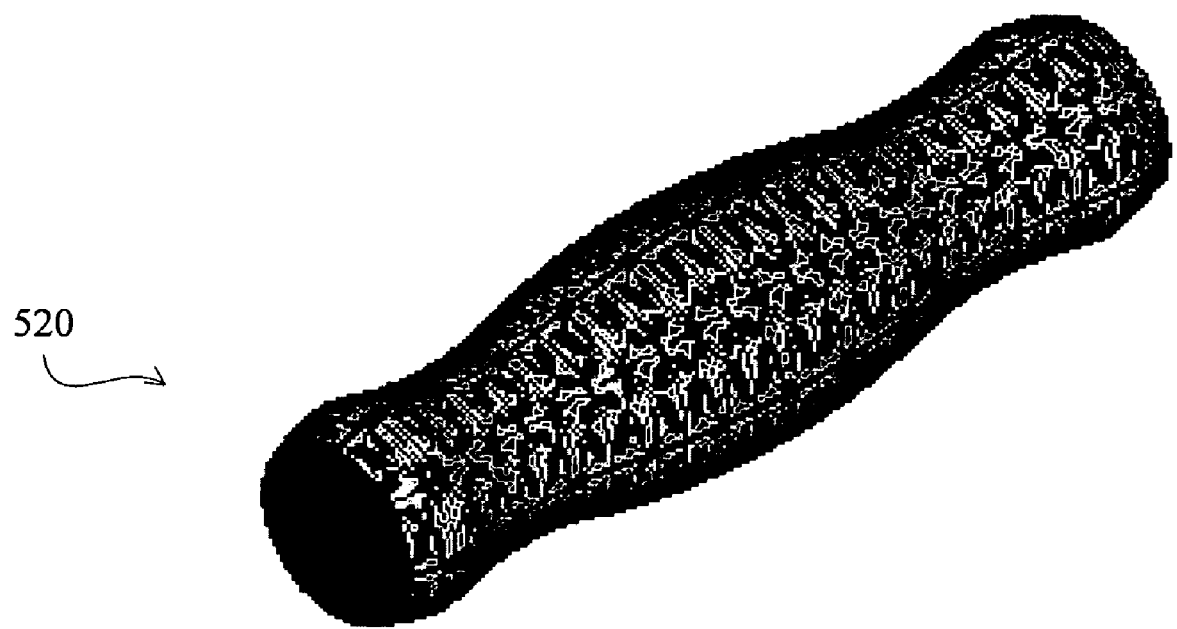
FIG. 5 is a diagram illustrating a stent formed using the mold of FIG. 11.
Figure 11:
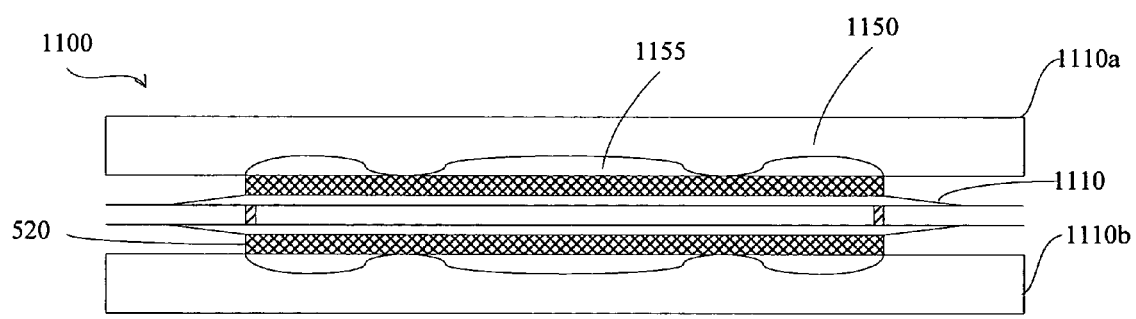
FIG. 11 is a diagram illustrating a cross section of a mold according another embodiment of the invention.

FIG. 5 depicts a stent 520 with an oscillating cross section formed using mold 1100 in FIG. 11. Stent 520 has a wave-like shape or profile, which provides the advantages mentioned above. It will be appreciated by one of ordinary skill in the art that stent 520 can take other wave profiles. For example, the profile can include additional crests and troughs and/or can be symmetrical or asymmetrical.

Various embodiments of a mold for implantable medical devices that are described herein may include a mold member having a mold bore configured to mold a stent mounted on a delivery system. The mold member may mold the stent after the delivery system expands an outer surface of the stent onto at least a portion of an inner surface that defines the mold bore.

A mold member may be composed of more than one piece. In some embodiments, the mold member may be composed of two halves. Each half may have a device-holding groove. The grooves may be configured to form the mold bore when the two halves are joined. In one embodiment, the mold may include a lock adapted to inhibit or prevent opening of the mold during molding of the device.

In one embodiment, a mold member may have a projection into a proximal section of a mold bore of the mold member. The projection may be configured to mold a tapered section at a proximal end of an implantable medical device, such as a stent, mounted on a delivery system. The tapered section, as described above, may be adapted to improve the attachment of the stent to the delivery system and facilitate the delivery of the mounted stent into and through a bodily lumen.

In another embodiment, the mold member may have a second projection into a distal section of a mold bore of the mold member for molding a tapered section into a distal end of a stent. In some embodiments, the projection may include a cylindrical member having an annulus disposed within the mold.

Figure 6:
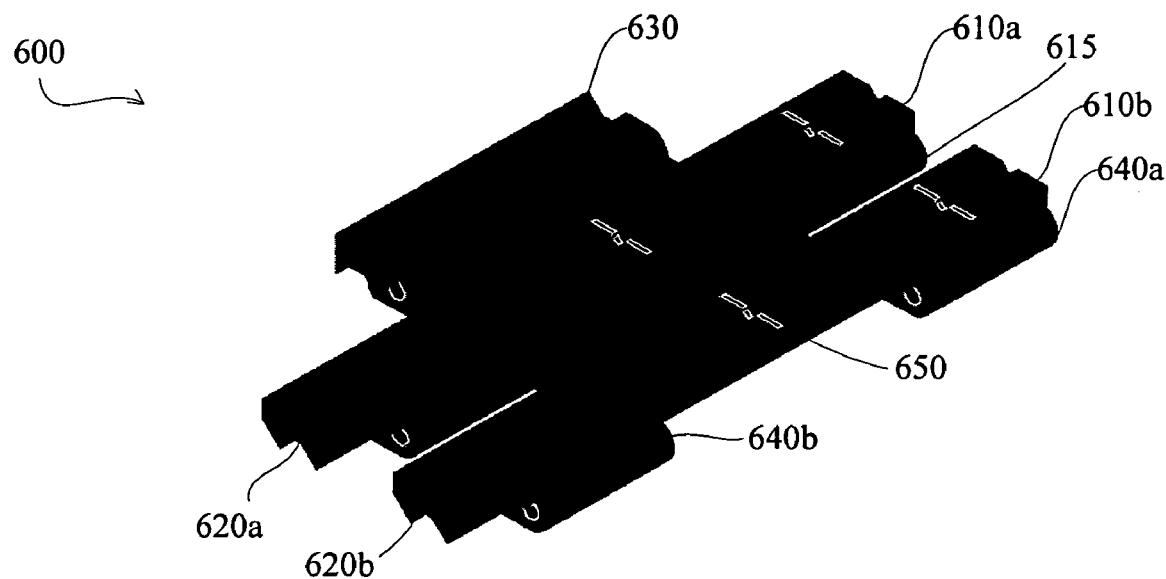
FIG. 6 is a diagram illustrating a mold according to an embodiment of the invention.

As an illustration, FIG. 6 is a diagram illustrating a mold member or mold 600 according to an embodiment of the invention that may, for example, mold stent 220 in FIG. 2. Mold 600 takes a split mold shape and has two halves: 610a and 610b, each having a groove 620a and 620b, respectively, running down a longitudinal axis of halves 610a and 610b. Halves 610a and 610b are coupled together via a hinge 615 that enables mold 600 to open and close via rotation of one half with respect to the other half. Hinge 615 ensures proper alignment of the halves 610a and 610b when mold 600 is closed. Grooves 620a and 620b are configured to receive and hold a balloon catheter 210 (FIG. 2) and a stent 220 (FIG. 2) in place.

Grooves 620a and 620b form a mold bore 625 (FIG. 7) through mold 600 when mold 600 is closed, that has a diameter greater than the diameter of stent 220 (e.g., from about 0.003 inches greater to about 0.048 inches greater for a stent which is approximately 0.045 inch in diameter). Grooves 620a and 620b each include two half washers 650 spaced apart to approximately match the length of stent 220. Half washers 650 project or extend into grooves 620a and 620b.

When balloon catheter 210 is expanded (via internal air pressure), balloon catheter 210 pushes against an inner surface of stent 220, causing stent 220 to expand to match the diameter of bore 625 formed by grooves 620a and 620b. However, since half washers 650 extend into grooves 620a and 620b, the proximal and distal ends of stent 220 cannot expand to the same diameter as the rest of the stent 220 (e.g., to the diameter of bore 625).

Accordingly, stent 220 has a profile after molding in which at least a portion of its proximal and distal ends are tapered inwards. The tapered inward edges facilitate smooth communication of stent 220 through a patient's vasculature without substantially limiting the ability of stent 220 to bend around curvatures in the vasculature. Further, the tapered ends tend to grip the balloon catheter 210 better than untapered ends, inhibiting or preventing stent 220 from disengaging from balloon catheter 210 before it is deflated.

Half 610a includes a first member 630 of a barrel locking mechanism. Half 610b includes a second and third member of the barrel locking mechanism 640a and 640b. Member 630 acts in combination with members 640a and 640b to lock mold 600 after placement of balloon catheter 210 and stent 220 into grooves 610a or 610b and closing mold 600. The barrel locking mechanism inhibits or prevents mold 600 from opening when balloon catheter 210 is expanding.

In alternative embodiments of the invention, different locking mechanisms can be used. Further, halves 610a and 610b need not be coupled together via hinge 615.

Figure 7:
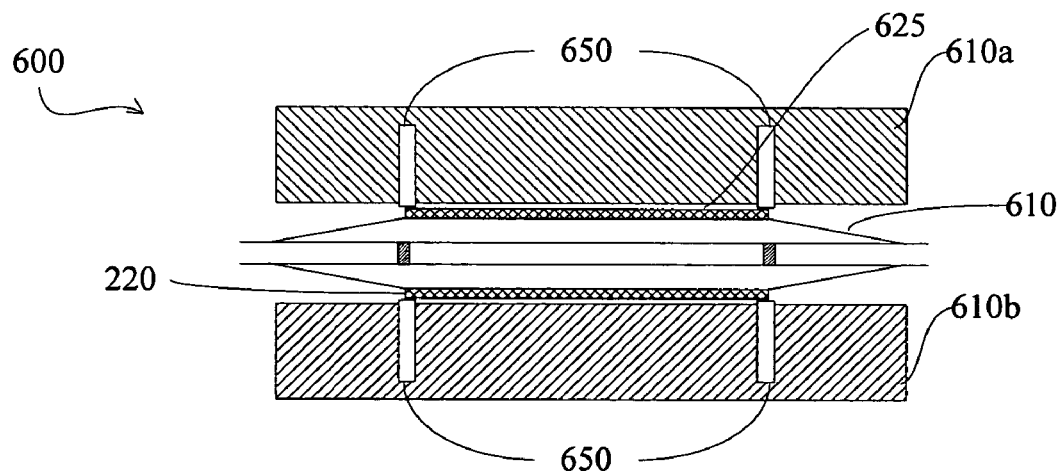
FIG. 7 is a diagram illustrating a cross section of the mold of FIG. 6.

FIG. 7 is a diagram illustrating a cross section of mold 600. Closing mold 600 forms bore 625 in which a mounted stent 220 is disposed. Mounted stent 220 is aligned with half washers 650 such that the distal end of the stent 220 is in alignment with a first pair of half washers 650 and the proximal end is in alignment with a second pair of half washers 650. Half washers 650 on the same mold half are spaced apart at a length equal to about the length of mounted stent 220. Half washers can extend several thousandths of an inch into the bore of the mold 600 (e.g., about 0.002 to about 0.005 inches, or more narrowly about 0.003 to about 0.004). Half washers can have a width of about 0.5 mm to about 4 mm or slightly less than half the length of the stent.

In an embodiment of the invention, mold 600 includes only a single pair of half washers 650 that are positioned at one end of stent 220, preferably the leading edge of stent 220 (i.e., the edge of stent 220 that faces the direction of travel during installation of stent 220). Accordingly, stent 220 would have a single tapered end that would facilitate deliverability of stent 220.

Once stent 220 is disposed within bore 625 of closed mold 600, balloon catheter 210 is heated and expanded. Specifically, balloon catheter 210 is heated up to about 190° F. to soften balloon catheter 210, thereby causing expansion (referred to as thermogripping). Internal pressure is supplied to the balloon catheter 210 to cause further expansion. Specifically, about 120 PSI to about 330 PSI, or more narrowly about 150 PSI to about 290 PSI, can be applied to cause expansion of catheter 210.

Expansion of balloon catheter 210 causes balloon catheter 210 to press against the inner diameter of stent 220. Expansion of balloon catheter 210 causes a majority of stent 220 to expand to the diameter of bore 625 of mold 600. Half washers 650 prevent ends of stent 220 aligned with the half washers 650 from expanding to the diameter of bore 625 of mold 600. As the ends of the stent 220 press against the half washers 650, the ends of the stent 220 are prevented from expanding, thereby yielding a stent profile with inward tapered ends.

In one embodiment, a mold bore may have a proximal section tapering inward to a proximal end of the mold bore and a distal section tapering inward to a distal end of the mold bore. The tapered sections may be adapted to mold tapered sections of the stent that improve the attachment of the stent to the delivery system and that facilitate the delivery of the mounted stent into and through a bodily lumen. In an embodiment, the mold bore may taper inward relatively uniformly between a proximal section and a distal section.

Figure 8:
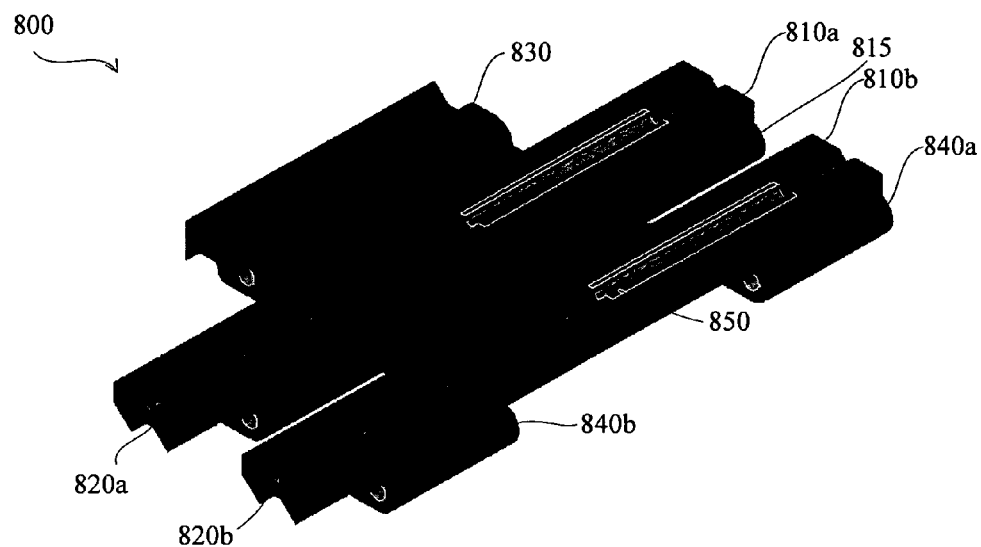
FIG. 8 is a diagram illustrating a mold according to another embodiment of the invention.

FIG. 8 is a diagram illustrating a mold 800 according to another embodiment of the invention. Mold 800 is substantially similar to mold 600 except that mold 800 includes a mold block 850 rather than washers 650. Specifically, mold 800 includes two mold halves 810a and 810b coupled together via a hinge 815. Half 810a includes a groove 820a having a mold block 850 and half 810b includes a groove 820b having a mold block 850. A barrel lock mechanism 830 is coupled to half 810a. Mechanism 830 acts in combination with barrel lock mechanisms 840a and 840b that are coupled to half 810b, to lock mold 800 shut after placement of a stent 520 within.

Figure 9:
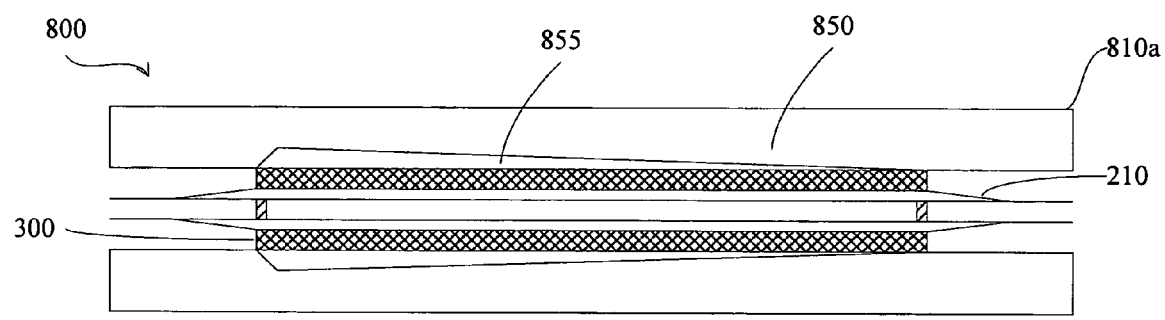
FIG. 9 is a diagram illustrating a cross section of the mold of FIG. 8.

FIG. 9 is a diagram illustrating an axial cross section of a mold 800 that may mold stent 300 depicted in FIG. 3. Mold block 850 (and a resulting stent 300 shown in FIG. 3 after balloon catheter 220 expands) has an arrow-like shape in which a mold bore 855 of mold block 850 tapers inward relatively uniformly from a proximal to a distal end of bore 855. The diameter of mold bore 855 of mold block 850 gradually increases from a distal end to a proximal end.

Delivery of the stent may be facilitated by having the distal end as the end of the stent that faces the direction of delivery. In one embodiment, the distal end or leading end may have a diameter of about 0.038 inches. The diameter may increase to a point proximate to the proximal end to a diameter of about 0.041 inches (e.g., at about 5.5 mm from the leading end in a 6 mm stent). At the proximal end, the diameter may taper off from about 0.041 inches to about 0.038 inches (from about 0.5 mm from the proximal end in a 6 mm stent).

In other embodiments, the mold bore may taper inward relatively uniformly from an intermediate point between a proximal end and a distal end to the proximal end. The mold bore may also taper inward relatively uniformly from the intermediate point to the distal end.

Figure 10:
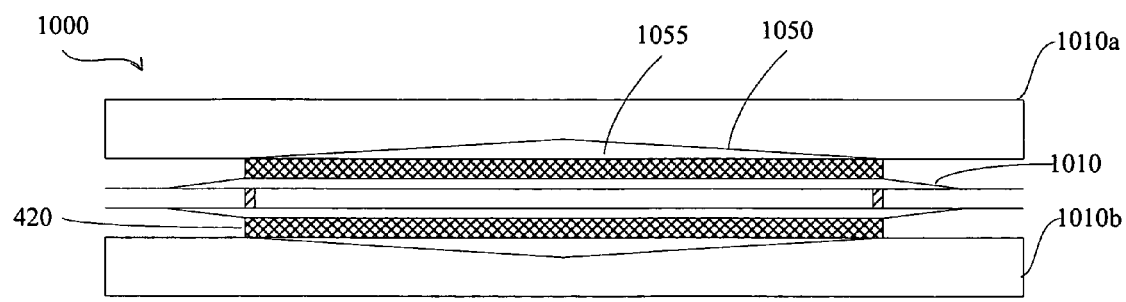
FIG. 10 is a diagram illustrating a cross section of a mold according another embodiment of the invention.

FIG. 10 is a diagram illustrating a cross section of a mold 1000 according another embodiment of the invention for molding stent 410 in FIG. 4. The mold 1000 is substantially similar to the mold 600 except that mold block 650 is replaced with a mold block 1050. Bore 1055 of mold block 1050 tapers inward from approximately a midpoint along bore 1055 toward both a distal and proximal end of bore 1055. The slope of the taper is such that expansion of a stent 420 in mold 1000 yields a stent 420 having a smaller diameter at the proximal and distal ends with a gradually increasing diameter to a maximum diameter at the middle of stent 420.

In a further embodiment, a mold bore of a mold member may have a section with a cross-section that oscillates in size between a proximal section and a distal section. The oscillating cross section may be configured to mold a stent mounted on a delivery system to have an oscillating cross section. The oscillating cross section of the stent may improve flexibility of the mounted stent during delivery.

FIG. 11 is a diagram illustrating a cross section of a mold 1100 according another embodiment of the invention for molding stent 520 in FIG. 5. Mold 1100 is substantially similar to the mold 600 except that a mold block 1150 replaces mold block 650. Mold block 1150 is approximately the length of stent 520. Bore 1155 of mold block 1150 has a diameter than varies along its length with larger diameter sections alternating with smaller diameter sections. As shown in FIG. 11, the inner surfaces of mold block 1150 have a wave-like profile. For example, in profile, the mold block 1150 can take the form of a sine wave. In an embodiment of the invention, bore 1155 of mold block 1150 can have three crests and four troughs, with troughs occurring at the proximal and distal ends.

In FIG. 11, mold block 1150 matches the length of the stent (e.g., about 6 mm) and features three crests and four troughs, wherein two troughs are aligned with the proximal and distal ends of the stent 520. Expansion of balloon catheter 210 causes stent 520 to take the shape of bore 1155 of mold block 1150, e.g., the stent 520 develops a wave profile, which secures stent 520 to balloon catheter 210 while maintaining flexibility and facilitating deliverability. The height variation between crests and troughs is a few thousands of an inch, e.g., about 0.001 to about 0.005 inches, or more narrowly, about 0.003 to about 0.004.

Figure 12:
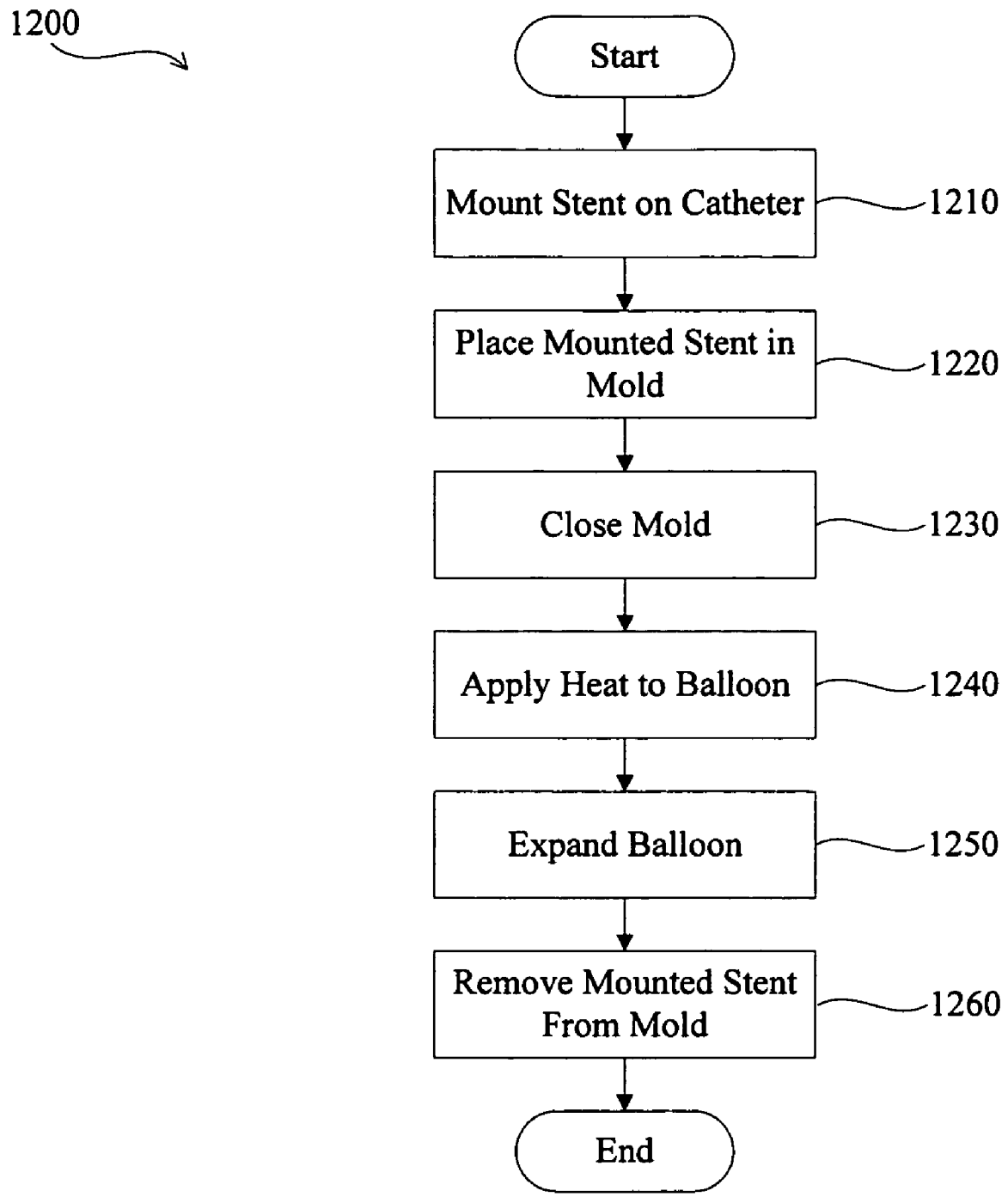
FIG. 12 is a flowchart illustrating a method of gripping a stent on a catheter according to an embodiment of the invention.

FIG. 12 is a flowchart illustrating a method 1200 of gripping a stent on a catheter according to an embodiment of the invention. First, a stent is mounted (1210) on a catheter, as is known to those of ordinary skill in the art. The mounted stent in then placed (1220) in a groove of a mold (e.g., the molds 600, 800, 1000 or 1100) and aligned with the washers or blocks. The mold is then closed (1230) and locked. Heat is then applied (1240) to the balloon catheter 210 to cause the balloon catheter 210 to soften and therefore more easily expand. In an embodiment of the invention, the heat can reach up to about 190° F. The balloon catheter 210 is then expanded (1250) by applying internal air pressure, e.g., about 120 PSI to about 330 PSI, or more narrowly about 150 PSI to about 290 PSI. During expansion, the balloon catheter 210 expands and presses into the stent, causing the stent to expand until the stent matches the diameter of the bore of the mold. The stent then takes on the shape of the mold. The mounted stent is then removed (1260) from the mold after the mold is unlocked.

In some embodiments, heat may facilitate expansion of the stent. Heat may be applied to the device and/or the delivery system prior to and/or during expanding the device. Heat may be applied by pumping heated fluid into a delivery system, such as balloon catheter. Alternatively heat applied by blowing a heated inert gas (e.g., air, nitrogen, oxygen, argon, etc.) onto the device and/or the delivery system.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A mold for a radially expandable stent, comprising:
a mold member having a projection into a proximal section of a mold bore of the mold member, wherein the projection comprises a disk-shaped portion of a washer extending into the mold bore, the projection configured to mold a tapered section at a proximal end of a stent mounted on a delivery system, the tapered section adapted to improve the attachment of the stent to the delivery system and facilitate the delivery of the mounted stent into and through a bodily lumen.

2. The mold of claim 1, further comprising a second projection into a distal section of a mold bore of the mold member.

3. The mold of claim 1, wherein the delivery system comprises a balloon catheter.

4. The mold of claim 1, wherein the mold member comprise two halves, each half having a stent-holding groove, the grooves configured to form the mold bore when the two halves are joined.

5. The mold of claim 1, wherein the washer is disposed within a cavity in the mold member.

6. The mold of claim 1, wherein a cylindrical axis of the washer is aligned with the cylindrical axis of the mold bore.

7. The mold of claim 4, wherein one half comprises a first locking member of a locking mechanism and the other half comprises second and third locking members of the locking mechanism, wherein the first locking member acts in combination with the second and third locking members to lock the mold member upon joining the two halves.

8. The mold of claim 2, wherein the projections are spaced apart about 4 mm to mold the tapered section at the proximal end of the stent and the tapered section at the distal end of the stent.

9. The mold of claim 1, wherein a width of the washer is between 0.5 mm to 4 mm.

10. The mold of claim 1, wherein the projection extends into the mold bore between 0.002 in and 0.005 in.

11. The mold of claim 1, wherein the washer comprises two separable half-washer halves disposed in two separable halves of the mold member.

* * * * *